United States Patent [19]

Yang et al.

[11] Patent Number: 5,422,406

[45] Date of Patent: Jun. 6, 1995

[54] RARE EARTH HOMOGENEOUS CATALYSTS FOR THE RING-OPENING POLYMERIZATION AND COPOLYMERIZATION OF STRAINED-RING OLEFINS

[75] Inventors: Xinmin Yang; Afif M. Seyam; Tobin J. Marks, all of Evanston, Ill.

[73] Assignee: Northwestern University, Evanston, Ill.

[21] Appl. No.: 189,988

[22] Filed: Feb. 1, 1994

Related U.S. Application Data

[63] Continuation-in-part of Ser. No. 962,390, Oct. 16, 1992, Pat. No. 5,300,598.

[51] Int. Cl.$^6$ ................................................ C08F 4/52
[52] U.S. Cl. ........................................ 526/126; 526/170; 526/308; 526/309
[58] Field of Search ............... 526/126, 134, 170, 308, 526/164, 309

[56] References Cited

U.S. PATENT DOCUMENTS

| | | | |
|---|---|---|---|
| 4,801,666 | 1/1989 | Marks et al. | 526/123 |
| 5,064,802 | 11/1991 | Stevens et al. | 526/170 X |
| 5,066,739 | 11/1991 | Pettijohn et al. | 526/127 |
| 5,066,741 | 11/1991 | Cambpell, Jr. | 526/171 |
| 5,132,369 | 7/1992 | Yasuda et al. | 526/170 X |
| 5,300,598 | 4/1994 | Marks et al. | 526/134 |

OTHER PUBLICATIONS

"Polymerisation du methyleneyclobutane Obtention de l'isocaoutchouc," Pinazzi, et al., Die Makromoleukulare Chemie, 147 (1971), pp. 15–33.

"Radical Polymerization of 3-Substituted-1-Methylenecyclobutanes," Hiraguri, et al., Journal of Polymer Science, vol. 26, (1988), pp. 381–384.

"L'Isocaoutchone, Etude des parametres de cyclisation et d'Isomerisation: " Pinazzi, et al., Die Makromolekulare Chemie, 148 (1971), pp. 81–82.

"Polymerization of Methylenecyclobutane, Synthesis of an Isopolyisoprene," Pinazzi, et al. Die Makromolekulare Chemie, 122 (1969), pp. 105–122.

"Vinylpolymerisation," Takemoto, et al., Die Makromolekulare Chemie, 109 (1967), pp. 81–86.

"On The Ring-Opening Polymerization of Methylenecyclobutane," Rossi, et al. Macromolecules, vol. 5, No. 3, (1972), pp. 247–249.

*Primary Examiner*—Fred Teskin
*Attorney, Agent, or Firm*—Welsh & Katz, Ltd.

[57] ABSTRACT

The organolanthanide hydrides $(Cp'_2LnH)_2$ ($Cp'=\eta^5$-$Me_5C_5$; $Ln=Sm, Lu$) rapidly catalyze the copolymerization of methylenecyclopropane and ethylene to cleanly yield high molecular weight polyolefins of microstructure $\{[CH_2CH_2]_x[CH_2CH_2C(CH_2)]_y\}n$ via sequential olefin insertion and ring-opening/$\beta$-alkyl shift processes. Homopolymerization of methylenecyclopropane likewise cleanly yields polymers of the structure $[CH_2CH_2C(CH_2)]_n$.

22 Claims, 2 Drawing Sheets

RARE EARTH HOMOGENEOUS CATALYSTS FOR THE RING-OPENING POLYMERIZATION AND COPOLYMERIZATION OF STRAINED-RING OLEFINS

BACKGROUND OF THE INVENTION

This invention was made with Government support under The National Science Foundation (Grant CHE9104112). The Government has certain rights under this contract.

This application is a continuation-in-part of application Ser. No. 962,390, filed Oct. 16, 1992, now U.S. Pat. No. 5,300,598.

This application relates to catalysts and more particularly to homogeneous catalysts for use in polymerization via the ring opening of strained ring systems.

In the presence of Ziegler-Natta catalysts, such as AlEt$_2$Cl-Cr(acac)$_3$ and Al(i-AlBu)$_3$-TiCl$_4$ARA, it is known that methylenecyclobutane (A) can be polymerized into a polymer consisting of a mixture of structure units B and C, through a ring-opening mechanism and a simple vinyl type insertion mechanism, respectively. Structure B is particularly interesting in that it imparts

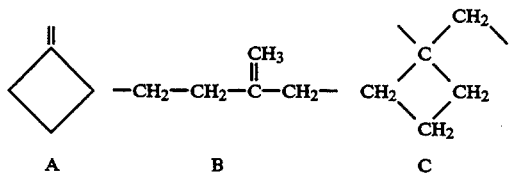

A        B        C useful functionalities into polyolefins. However, the activity of these catalysts are extremely sluggish.

In U.S. application Ser. No. 962,390 a new class of homogeneous group 4 metal-based catalysts was disclosed to catalyze the ring-opening polymerization of A into B with both much higher activity and selectivity. Furthermore, these homogeneous catalysts can also effectively copolymerize A and simple olefins such as ethylene and propylene to form copolymers containing a broad range of exomethylene functionalities, with a general formula $\{-(CH_2CHR)_x-[CH_2CH_2CH_2C(CH_2)]_y-\}_n$. These catalysts can be generally represented as $L_1L_2MR^+X^-$, where $L_1$ and $L_2$ are cyclopentadienyl or substituted cyclopentadienyl ligands; M is a metal selected from Ti, Zr and Hf; R is a hydrogen or a alkyl radical with 1-20 carbon atoms; $X^-$ is a charge-compensating anion selected from $R'B(C_6F_5)_3^-$, $B(C_6F_5)_4^-$, or methylalumoxane. The homo- and co-polymers formed using the homogeneous catalysts have been characterized by $^1H/^{13}C$ NMR spectroscopy and GPC analysis.

Lanthanide complexes of the types $(C_5Me_5)_2LnR$ and $(Me_2Si)(C_5Me_4)_2LnR$, where Ln is a metal chosen from the lanthanide series in The Periodic Table, or Sc and Y; R is hydrogen or an alkyl radical, are a unique class of complexes and have been shown to be efficient catalysts for a variety of chemical transformations including the polymerization of simple olefins such as ethylene and propylene.

SUMMARY OF THE INVENTION

Therefore, an object of the subject invention is a novel catalyst for polymerizations having high activity.

A further object of the subject invention is a catalyst for olefin polymerization which operates via a ring-opening mechanism.

A still further object of the subject invention is a catalyst by which electrophilic lanthanide catalysts catalyze the facile regioselective ring-opening homopolymerization of exomethylene substituted cyclic organic compounds and the copolymerization of such compounds with olefins such as ethylene, propylene and styrene via a β-alkyl shift mechanism.

Rare earth homogeneous complexes of the type $(Cp'_2LnH)_2$ (Ln=Sm, Lu; Cp' is a cyclopentadienyl-containing ligand such as $\eta^5$-C$_5$Me$_5$) can efficiently catalyze the copolymerization of simple olefins and methylenecyclopropane to form exomethylene functionalized polyolefins with the general structure $\{-(CH_2CHR)_x-[CH_2CH_2C(CH_2)]_y-\}$, where R is H, CH$_3$ or Ph when the olefin is ethylene, propylene or styrene, respectively. The Lu catalysts also effect the homopolymerization of methylecyclopropane to form $[-CH_2CH_2C(CH_2)-]_n$. The key step in these polymerization processes is a lanthanide-mediated β-alkyl shift ring-opening process. Such a ring-opening polymerization process should be applicable to the polymerization of a variety of strained ring monomers having exocyclic unsaturation.

BRIEF DESCRIPTION OF THE DRAWINGS

These and other objects of the subject invention are more apparent from the following detailed description when taken in conjunction with the accompanying drawings wherein.

DETAILED DESCRIPTION OF THE INVENTION

Facile β-alkyl transpositions are a distinctive feature of electrophilic $d^0f^n$ hydrocarbyl chemistry (e.g., equation (I)) and

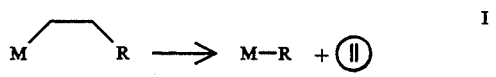

I represent an important chain transfer channel in certain olefin polymerization processes. In principle, such transpositions might also provide an unusual pathway to functionalized polyolefins by coupling olefin insertion and strained monomer ring-opening sequences (equation (II)).

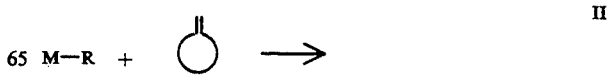

II

-continued

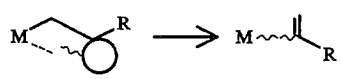

The exo-methylene cyclic organic compounds may be represented by the general formula D:

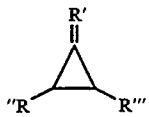

where R', R'', and R''' are hydrogen, aryl or alkyl groups (C=1–10) which may also include O, N, S or P. Preferably, the monomer is methylenecyclopropane.

The simple olefin used in the copolymerization can be ethylene or other α-olefins such as propylene, 1-hexene or styrene.

The lanthanide catalysts used can be represented as $[\eta^5\text{-}R^1R^2R^3R^4R^5C_5]_2LnR^6$, where $R^{1-6}$=an alkyl (1–20 carbons), aryl, or hydride group; one of $R^1$, $R^2$, $R^3$, $R^4$, $R^5$, can be an organic or organometallic group which bridges the two cyclopentadienyl-type rings (e.g.; $Me_2Si$); Ln is a metal chosen from the lanthanide series in The Periodic Table, Sc, and Y.

Copolymerization of D with olefins such as ethylene, propylene and styrene, etc. can be readily effected by stirring D neat or in a diluent such as toluene, or other hydrocarbon at −78° C. in the presence of the comonomer at a temperature from 0°–100° C. and quenching, preferably preferably with an alcohol, such as methanol. $^1H$ and $^{13}C$ NMR spectroscopy indicates that the derived copolymers have ring-opened microstructure D exclusively and that the x and y proportions can be controlled via the reaction stoichiometry.

The proposed reaction mechanism for the copolymerization is shown below:

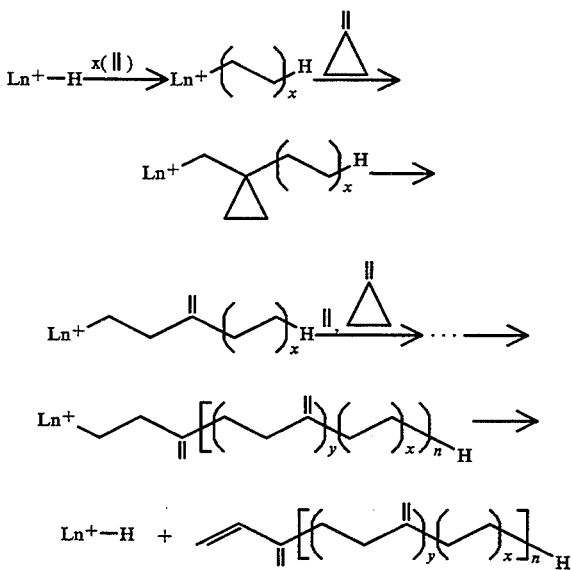

Figure 2A:
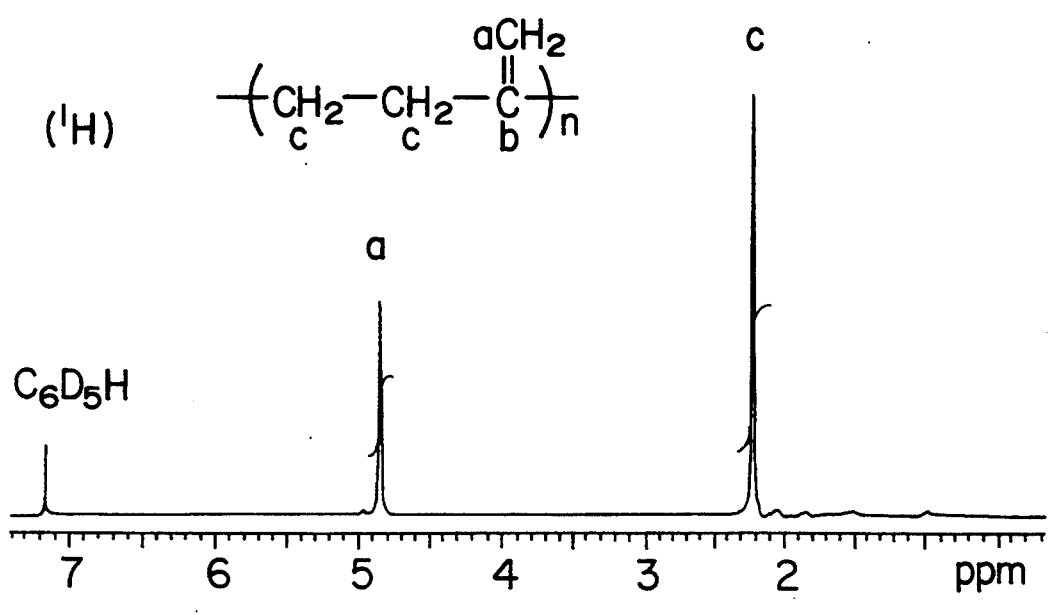
FIG. 2(a) is the $^1$H NMR spectra (400 MHz, benzene-d$_6$) of a (Cp'$_2$LuH)$_2^-$ catalyzed methylenecyclopropane homopolymer.
Figure 2B:
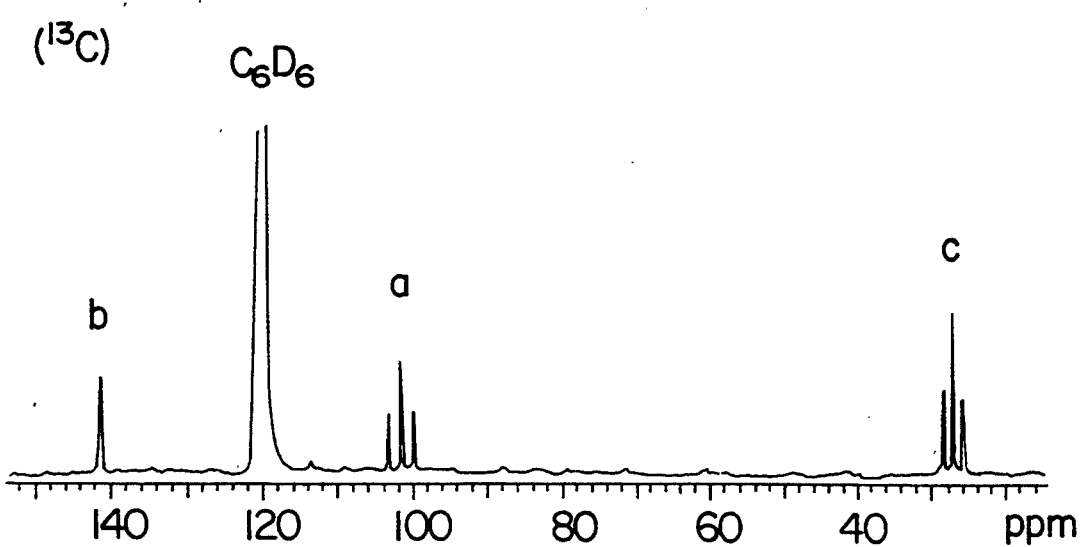
FIG. 2(b) is the $^{13}$C NMR spectra (100 MHz, benzene-d$_6$) of (Cp$_2$'LuH)$_2^-$ catalyzed methylenecyclopropane homopolymer.

The homopolymerization of methylenecyclopropane by the lanthanide catalysts according to the subject invention, shows some very unusual behavior. For instance, $(Cp'_2LuH)_2$ can homopolymerize methylenecyclopropane very selectively through a ring-opening mechanism. The structure of the resulting polymer has been confirmed by $^1H$ and $^{13}C$ NMR spectroscopy (FIG. 2). However, the yield of the polymer per unit amount of catalyst is very low compared to the analogous polymerization of methylenecylobutane by the zirconium catalysts. The polymerization stops even though there is still a large amount of monomer left. However, this is not a result of poisoning by any impurity in the reaction media. This phenomenum could be demonstrated by the observation that when ethylene is added to such a reaction system, very fast copolymerization then occurs. From the reaction chemistry of such lanthanide catalysts it is believed that some kind of metal allyl species like Reaction Sequence III is formed during the homopolymerization process.

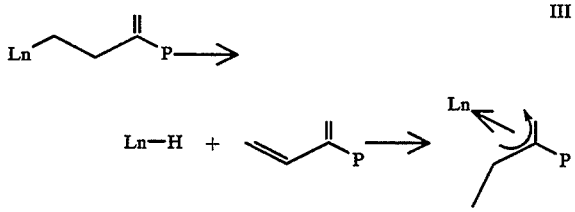

Such an allylic complex cannot react further with the bulky methylenecyclopropane but can react with the smaller ethylene.

Examples

All operations were performed with rigorous exclusion of oxygen and moisture in flamed Schlenk-type glassware in a dual manifold Schlenk line or interfaced to a high vacuum ($10^{-5}$ torr) system, or in a nitrogen or argon filled glovebox with a high capacity atmosphere recirculator. Argon, ethylene and propylene were purified by passage through a supported MnO oxygen removal column and a molecular sieve column. Aliphatic hydrocarbon solvents were pretreated with concentrated $H_2SO_4$, $KMnO_4$ solution, $MgSO_4$ and Na, 4 Å molecular sieves. All reaction solvents were distilled from Na/K/benzophenone under nitrogen and were condensed and stored in vacuo in bulbs on the vacuum line containing a small amount of $[Ti(\eta^5\text{-}C_5H_5)_2Cl]_2ZnCl_2$ as indicator. Methylenecyclopropane was additionally dried over Na/K.

Catalyst Syntheses

In general or $Cp_2'MCHTMS_2$ complexes may be prepared by mixing approximately equimolar amounts of the corresponding $Cp'_2LnCl_2Li(ether)_2$ complex and $LiCHTMS_2$ as appropriate, in toluene for 8–16 hours (preferably 12 hours) at −10° C. to 25° C. (preferably 0° C.). The solvent is then removed and the residue extracted with another solvent, preferably pentane. The extract is cooled to recrystallize the $Cp_2'MCHTMS_2$ complex.

EXAMPLE 1

$Cp_2'LuCHTMS_2$

The aforementioned procedure set forth above was carried out with 3.1 g $Cp'_2LuCl_2Li(ether)_2$ and 0.79 g $LiCHTMS_2$ ($LiCH[Si(CH_3)_3]_2$) in 150 mL of toluene. The standard workup and pentane recrystallization yielded 1.8 g (64%) of $Cp_2'LuCHTMS_2$.

(Cp$_2$'MH)$_2$ compounds may be prepared by stirring CP$_2$'MCHTMS$_2$/pentane under a hydrogen atmosphere for 0.1-2.5 hours, preferably 2 hours) at a temperature of $-10°$ C. to $10°$ C. (preferably $0°$ C.). The resulting precipitate may be isolated by filtration, washing and the like.

EXAMPLE 2

(Cp$_2$'LuH)$_2$

Cp$_2$'LuCHTMS$_2$ or Cp$_2$'LuCH[Si(CH$_3$)$_3$]$_2$ (1.0 g) was stirred under and H$_2$atmosphere in 50 mL of pentane for 2 hours at $0°$ C. The resulting colorless precipitate was isolated by filtration, washed with $2\times 3$ mL pentane, and dried in vacuo to yield 0.72 g (98%) (Cp$_2$'LuH)$_2$ as a microcrystalline solid.

EXAMPLE 3

(Cp$_2$'SmH)$_2$

Cp$_2$'SmCHTMS$_2$or Cp$_2$'SmCH[Si(CH$_3$)$_3$]$_2$ (1.0 g) was stirred under and H$_2$ atmosphere in 50 mL of pentane for 2 hours at $0°$ C. The resulting colorless precipitate was isolated by filtration, washed with $2\times 3$ mL pentane, and dried in vacuo to yield 0.65 g (90%)(Cp$_2$'SmH)$_2$ as a pink powder.

EXAMPLE 4

Copolymerization of ethylene and methylenecyclopropane.

In a typical copolymerization experiment, 15 mg of the catalyst (Cp'$_2$LnH$_2$)$_2$ was loaded into a 50 mL flask in the glove box. On the vacuum line, 20 mL of toluene and a measured amount of methylenecyclopropane at $-78°$ C. were then condensed into the flask. The reaction mixture was exposed to 1 atm of ethylene and stirred at room temperature with a constant bubbling of ethylene. The reaction was quenched by the addition of a small amount of methanol. The polymer was collected by suction filtration, washed with acetone three times, dried under vacuum for 12 h. The polymer product was characterized by H NMR spectroscopy and GPC. Different ratios of methylenecyclopropane with ethylene result in the data of Table I.

resulting polymer was characterized by $^1$H and $^{13}$C NMR spectroscopy.

Figure 1:
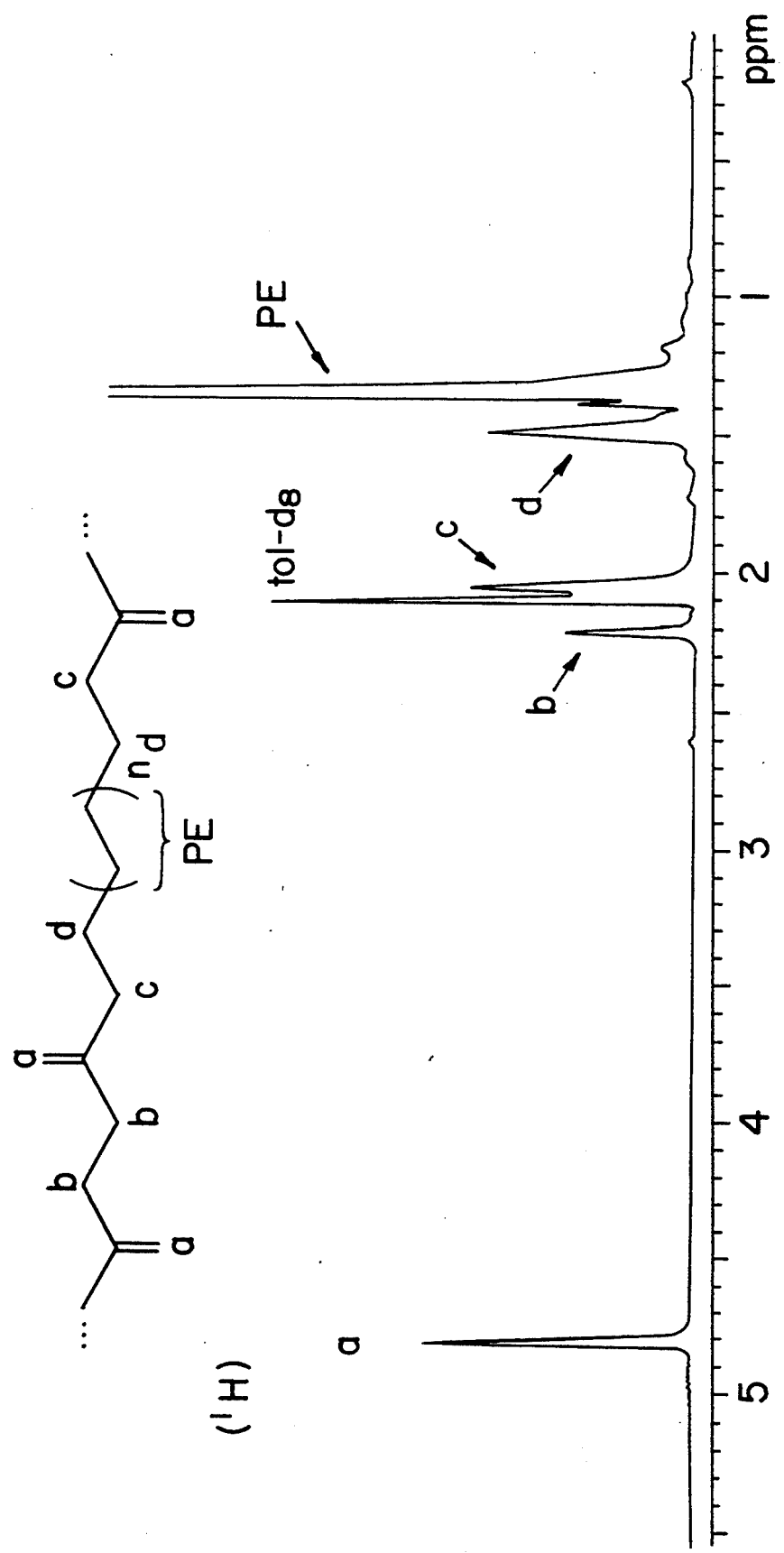
FIG. 1 is the $^1$H NMR spectrum (400 MHz, toluene-d$_8$) of the ethylene-methylenecyclopropane copolymer from entry 4, Table I.

From Table 1 both the samarium and lutetium catalysts are shown to be highly active for the copolymerization of ethylene and methylenecyclopropane to give high molecular weight polymers. The fairly high molecular weight also suggests that it is not significantly affected by the incorporation of such a monomer. The molecular weight distribution of about 2 is typical of homogeneous catalysts having similar active centers. Most importantly, the incorporation of exo-methylene functional groups in the copolymers is confirmed by the presence of a sharp signal at $\delta=4.8$ ppm in the $^1$H NMR spectrum (FIG. 1). The lack of any peaks in the region of 0.1-0.5 ppm in the above spectrum suggests that there is no "ring-unopened" unit (cyclopropane) in the copolymer. In addition, since a relatively high concentration of methylenecyclopropane was used in the copolymerization process (Entry 4, Table 3), peaks can be seen in the NMR spectrum that result from two (or more) ring-opened methylenecyclopropane monomers neighboring to each other.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

We claim:

1. A process for the ring-opening polymerization of exomethylene-containing cyclic hydrocarbons comprising: (a) providing a catalyst of the formula [$\eta^5$-R$^1$R$^2$R$^3$R$^4$R$^5$C$_5$]$_2$LnR$^6$, where R$^{1-6}$=an alkyl (1-20 carbons), aryl, or hydride group; one of R$^1$, R$^2$, R$^3$, R$^4$, R$^5$, can be an organic or organometallic group which bridges the $\eta^5$R$^1$R$^2$R$^3$R$^4$R$^5$C$_5$ ligands; Ln is a metal chosen from the group consisting of the lanthanide series, Sc, and Y; (b) contacting said catalyst with said exomethylene-containing cyclic olefin in a solvent and stirring at $0°$-$100°$ C., and collecting the polymeric product.

TABLE 1

Copolymerization of Methylenecyclopropane with Ethylene Using (Cp'$_2$LnH)$_2$(Ln = Sm,Lu) Catalyst

| Entry | Catalyst Amount (umol) | Methylene-cyclopropane (mL) | Ethylene Pressure (atm) | Reaction Time (h) | Yield of Polymer (g) | Activity (g polymer/ Mol Ln h) | Number of exo-methylenes per 1000-CH$_2$-Unit | M$_w$(M$_n$)$^c$ $\times$1000 |
|---|---|---|---|---|---|---|---|---|
| 1 | 21.4 (Sm) | 0.25 | 1.0 | 0.10 | 0.42 | 2.0 $\times$ 10$^5$ | 4.2 | 13(7) |
| 2 | 21.4 (Sm) | 0.50 | 1.0 | 0.17 | 0.45 | 1.2 $\times$ 10$^5$ | 6.7 | 184(42) |
| 3 | 33.6 (Lu) | 0.50 | 1.0 | 0.10 | 0.60 | 1.8 $\times$ 10$^5$ | 40 | 92(26) |
| 4 | 33.6 (Lu) | 2.50 | 1.0 | 0.10 | 0.47 | 1.4 $\times$ 10$^5$ | 91 | 3(2) |

$^a$Monomer conversion by $^1$H NMR.
$^b$Ratio of methylenecyclopropane and ethylene (per 1000 CH unit) incorporated into the copolymer as determined by $^1$H NMR.
$^c$By GPC versus polystyrene.

EXAMPLE 5

Homopolymerization of methylenecyclopropane at $-78°$ C. by (Cp'$_2$LuH)$_2$.

To a J-Young NMR tube, 10 mg. of the catalyst was loaded in the glove box. Then deuterated solvent (C$_6$D$_6$ or toluene-d$_8$) and a suitable amount of methylenecyclopropane were condensed into the NMR tube. It was allowed to react at room temperature. The 2. The process of claim 1, where said solvent is a hydrocarbon.

3. The process of claim 2, wherein said exomethylene-containing cyclic hydrocarbon is:

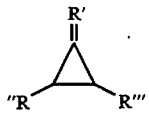

Where R" and R'" are selected from the group consisting of H, hydrocarbyl (1-10 carbons), and groups containing a heteroatom selected from the group consisting of O, S, N, P and R' is a methylene radical.

4. The method of claim 1 wherein one of $R^1$, $R^2$, $R^3$, $R^4$, $R^5$ and $R^6$ is $Me_2Si$.

5. The process of claim 3, where said catalyst is $(Cp'_2LnH)_2$ ($Cp'=\eta^5\text{-}C_5Me_5$; Ln = Sm, Lu).

6. The process of claim 3, where said solvent is toluene.

7. The process of claim 3, where said exomethylene-containing cyclic olefin is methylenecyclopropane.

8. A process for the copolymerization of olefins with an exomethylene-containing cyclic olefin comprising the steps of:
  (a) providing a catalyst of the formula $[\eta^5\text{-}R^1R^2R^3R^4R^5C_5]_2LnR^6$, where $R^{1-6}$ = an alkyl (1-20 carbons), aryl, or hydride group; one of $R^1$, $R^2$, $R^3$, $R^4$, $R^5$ can be an organic or organometallic group which bridges the $\eta^5\text{-}R^1R^2R^3R^4R^5C_5$ ligands; Ln is a metal chosen from the group consisting of the lanthanide series, Sc, and Y;
  (b) contracting said catalyst with an exomethylene-containing cyclic olefin in a diluent, and stirring at 0°-100° C. in the presence of a olefin, quenching the reaction and collecting the polymeric product.

9. The process of claim 8, where said olefin is CHR'=CR"R'", where R', R" and R'" is selected from the group consisting of H, or alkyl (1-20 carbons) or aryl.

10. The process of claim 9 where said diluent is a hydrocarbon solvent.

11. The process of claim 9, where said exomethylene-containing cyclic olefin is:

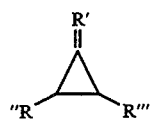

Where R" and R'" are selected from the group consisting of H, hydrocarbyl (1-10 carbons), and a group containing a heteroatom selected from the group consisting of O, S, N, P and R' is a methylene radical.

12. The process of claim 11, where said catalyst is $(Cp'_2LnH)_2$ ($Cp'=\eta^5\text{-}C_5Me_5$; Ln = Sm, Lu).

13. The process of claim 10, where said diluent is toluene.

14. The process of claim 11, where said exomethylene-containing cyclic olefin is methylenecyclopropane.

15. The process of claim 10, where said olefin is ethylene.

16. The process of claim 8 wherein said organic or organometallic group is $Me_2Si$.

17. A method for the polymerization of olefins comprising the steps of adding toluene and methylenecyclopropane at a temperature of about −78° C. to a flask containing a catalyst of the formula $(Cp'_2MH)_2$, stirring at 20° C., quenching with methanol and recovering the polymerized product, where Cp' = a cyclopentadienyl-containing ligand and M = Lu or Sm.

18. A method for the copolymerization of olefins comprising the steps of adding a solvent and methylenecyclopropane at a temperature of about −78° C. to a flask containing a catalyst, said catalyst comprising $(Cp'_2MH)^2$, where Cp' = a cyclopentadienyl-containing ligand, M = Lu, Sm, adding an α-olefin, stirring, quenching and recovering the polymer product.

19. The method of claim 18 wherein said solvent is a nonpolar organic solvent.

20. The method of claim 19 wherein said solvent is selected from the group consisting of aliphatic and aromatic hydrocarbons.

21. The method of claim 20 wherein said solvent is toluene.

22. The method of claim 18 wherein said α-olefin is ethylene, propylene, butylene or styrene.

* * * * *